United States Patent
Jordan et al.

(10) Patent No.: US 8,771,657 B2
(45) Date of Patent: Jul. 8, 2014

(54) PERSONAL CARE COMPOSITIONS WITH ETHYLENE ACRYLIC ACID COPOLYMER AQUEOUS DISPERSIONS

(75) Inventors: Susan L. Jordan, Doylestown, PA (US); Tatiana V. Drovetskaya, Basking Ridge, NJ (US)

(73) Assignee: Union Carbide Chemicals & Plastics Technology LLC, Midland, MI (US)

( * ) Notice: Subject to any disclaimer, the term of this patent is extended or adjusted under 35 U.S.C. 154(b) by 263 days.

(21) Appl. No.: 12/882,325

(22) Filed: Sep. 15, 2010

(65) Prior Publication Data

US 2011/0064683 A1    Mar. 17, 2011

Related U.S. Application Data

(60) Provisional application No. 61/242,490, filed on Sep. 15, 2009, provisional application No. 61/353,372, filed on Jun. 10, 2010.

(51) Int. Cl.
| | | |
|---|---|---|
| *A61Q 5/12* | (2006.01) |
| *A61K 8/04* | (2006.01) |
| *A61K 8/36* | (2006.01) |
| *A61Q 19/10* | (2006.01) |
| *A61K 8/368* | (2006.01) |

(52) U.S. Cl.
CPC ... *A61Q 5/12* (2013.01); *A61K 8/04* (2013.01); *A61Q 19/10* (2013.01); *A61K 8/368* (2013.01)
USPC ............... 424/70.11; 514/574; 424/78.37

(58) Field of Classification Search
None
See application file for complete search history.

(56) References Cited

U.S. PATENT DOCUMENTS

| | | |
|---|---|---|
| 4,599,392 A | 7/1986 | McKinney et al. |
| 4,701,432 A | 10/1987 | Welborn, Jr. |
| 4,988,781 A | 1/1991 | McKinney et al. |
| 5,272,236 A | 12/1993 | Lai et al. |
| 5,322,728 A | 6/1994 | Davey et al. |
| 5,384,373 A | 1/1995 | McKinney et al. |
| 5,935,561 A | 8/1999 | Inman et al. |
| 6,221,817 B1 | 4/2001 | Guskey et al. |
| 6,525,157 B2 | 2/2003 | Cozewith et al. |
| 6,627,184 B2 | 9/2003 | Coffindaffer et al. |
| 6,696,067 B2 | 2/2004 | Brandt et al. |
| 6,960,635 B2 | 11/2005 | Stevens et al. |
| 7,303,744 B2 | 12/2007 | Wells et al. |
| 7,314,904 B2 | 1/2008 | Nadolsky et al. |
| 2003/0091512 A1 | 5/2003 | Adjei et al. |
| 2003/0109391 A1 | 6/2003 | Midha et al. |
| 2004/0068805 A1 * | 4/2004 | Fishman ........................ 8/406 |
| 2006/0127345 A1 | 6/2006 | Hilvert et al. |
| 2007/0141323 A1 | 6/2007 | Wevers et al. |
| 2007/0295465 A1 * | 12/2007 | Dyer et al. ................... 162/111 |
| 2008/0020057 A1 | 1/2008 | Niebauer et al. |
| 2008/0072206 A1 | 3/2008 | Drasny et al. |
| 2010/0310671 A1 * | 12/2010 | Malotky et al. ............... 424/501 |

FOREIGN PATENT DOCUMENTS

WO    WO 2009064739 A1 *    5/2009

* cited by examiner

*Primary Examiner* — Robert A Wax
*Assistant Examiner* — Sarah Park
(74) *Attorney, Agent, or Firm* — Edward L. Brant

(57) ABSTRACT

Described are personal care compositions, comprising an aqueous dispersion comprising an ethylene acrylic acid copolymer and a least one cosmetically acceptable surfactant, emollient, or cosmetic active.

10 Claims, No Drawings

PERSONAL CARE COMPOSITIONS WITH ETHYLENE ACRYLIC ACID COPOLYMER AQUEOUS DISPERSIONS

CROSS-REFERENCE TO RELATED APPLICATION(S)

This application claims benefit of priority from U.S. Provisional Patent Application No. 61/242,490, filed Sep. 15, 2009, and U.S. Provisional Patent Application No. 61/353,372, filed Jun. 10, 2010, which applications are incorporated by reference herein in its entirety.

FIELD

The present application relates to personal care compositions.

BACKGROUND

Conditioning of hair and/or skin is one of the most desired attributes in a personal care composition, particularly conditioners, shampoos, and body washes. Cationic polymers are known to provide conditioning benefits, but can tend to build up on hair and cause limp and/or unmanageable hair. Other conditioning agents containing oily (silicone) or waxy (fatty acids) material are known, but have several drawbacks, including the proclivity of silicones to wash off the hair when paired with surfactants. Thus, it is important in the art to develop new non-cationic conditioning agents and formulations that offer similar aesthetic properties to silicones.

Likewise, there is a need for a conditioning shampoo that can clean, condition, and increase manageability, for example, exhibit improved curl retention and frizz control (that is, a reduction in the appearance or intensity of frizz, a term of art referring to an aesthetically undesirable appearance of individual hair fibers behaving independently and non-uniformly, whether from static, humidity, or damage).

SUMMARY

In one embodiment, the present invention provides personal care compositions, comprising an aqueous dispersion comprising an ethylene acrylic acid copolymer and a least one cosmetically acceptable surfactant, emollient, or cosmetic active.

DETAILED DESCRIPTION

In one embodiment, the present invention provides personal care compositions, comprising an aqueous dispersion comprising an ethylene acrylic acid copolymer and a least one cosmetically acceptable surfactant, emollient, or cosmetic active.

"Personal care" relates to compositions to be topically applied to a person (including mouth, ear, and nasal cavities, but not ingested). Examples of personal care compositions include skin care products (e.g., facial cream, moisturizers, leave on and rinse off lotions, sunscreens, foundation, mascara, eye-liner, lipstick, cleansers, and the like) and hair care products (including shampoos, leave on and rinse off conditioners, styling gels and hairsprays). Preferably, the personal care composition is a shampoo, a rinse-off conditioner, a leave-in conditioner, or a body wash. Preferably, the personal care composition is not an emulsion.

"Cosmetically acceptable" refers to ingredients typically used in personal care compositions, and is intended to underscore that materials that are toxic when present in the amounts typically found in personal care compositions are not contemplated as part of the present invention.

Copolymerizing ethylene with acrylic acid yields ethylene-acrylic acid (EAA) copolymers, which are known as flexible thermoplastics for blister packaging and the like. A preferred ethylene acrylic acid copolymer comprises greater than about 15 wt % acrylic acid, preferably greater than about 17 wt % acrylic acid, more preferably about 20 wt % acrylic acid. It should be understood that ranges recited in this disclosure include all subcombinations of ranges.

A preferred EAA copolymer is PRIMACOR 5990 copolymer (20 wt % acrylic acid), which has a melt index of 1300 g/10 minute (ASTM Method D-1238 at 190° C.) and a Brookfield viscosity of 13,000 cps at 350° F., and is available from The Dow Chemical Company. Another preferred EAA copolymer is PRIMACOR 5980i copolymer (20.5 wt % acrylic acid), which has a melt index of 300 g/10 minute (ASTM Method D-1238 at 190° C.), available from The Dow Chemical Company. EAA copolymers are also available under the tradename NUCREL 2806, available from E.I. du Pont de Nemours and Company, Inc. Ethylene-acrylic acid and ethylene-methacrylic acid copolymers, are described in U.S. Pat. Nos. 4,599,392, 4,988,781, and 5,938,437, each of which is incorporated herein by reference in its entirety.

Mechanical dispersion, such as a Parr reactor, is used to create the aqueous dispersion.

In one embodiment, the solids content of the aqueous dispersion is in a range from about 10% by weight to about 30% by weight, preferably about 20% by weight.

In turn, the aqueous dispersion is present in a range from about 0.05 wt % to about 10 wt % of solids, preferably about 0.25 wt % to about 5 wt %, by weight of the personal care composition.

The ethylene acrylic acid copolymer is present in a range from about 15 wt % to about 60 wt % of solids by weight of the aqueous dispersion.

It is understood that the aqueous dispersion comprising an ethylene acrylic acid copolymer can include additional components, for example, at least one anti-dandruff active (zinc pyrithione, salicylic acid, or selenium compounds), sunscreen actives (organic or inorganic), pigment, fragrance, botanical, amino acid, or vitamin.

In a preferred embodiment of the present invention, the aqueous dispersion comprises an ethylene acrylic acid copolymer and a metallocene catalyzed polyolefin. Typically, the ethylene acrylic acid copolymer and metallocene catalyzed polyolefin is in a polymer ratio of about 40:60 to about 15:85. In these embodiments, the solids content of the aqueous dispersion is in a range from about 30% by weight to about 50% by weight, preferably about 40% by weight. The ethylene acrylic acid copolymer is present in a range from about 15 wt % to about 60 wt % of the solids by weight of the aqueous dispersion, preferably in a range from about 35 wt % to about 45 wt % of the solids. This correlates to ethylene acrylic acid copolymer being present in a range from about 1 wt % to about 25 wt % by weight of the aqueous dispersion, preferably in a range from about 5 wt % to about 20 wt %.

Metallocene catalyzed polyolefins are polyolefins produced with a metallocene catalyst as described in U.S. Pat. Nos. 4,701,432, 5,322,728, and 5,272,236, each of which is incorporated herein by reference in its entirety. As a specific embodiment of the present invention, the metallocene catalyzed polyolefins are polyethylenes produced with a metallocene catalyst. Such metallocene catalyzed polyethylenes are available e.g. from The Dow Chemical Company under the trademark AFFINITY or ENGAGE (ethylene/octene copolymers) and from Exxon Chemical Company under the trademark EXACT (ethylene/butene copolymers, ethylene/hexene copolymers, or ethylene/butene/hexene terpolymers). In one embodiment, the metallocene catalyzed polyolefin is at least one of ethylene/octene copolymers, ethylene/butene copolymers, ethylene/hexene copolymers, ethylene/propylene or ethylene/butene/hexene terpolymers, preferably an ethylene octene copolymer. In another embodiment, the metallocene catalyzed polyolefin is a propylene/alpha-olefin copolymer, which is further described in details in the U.S. Pat. Nos. 6,960,635 and 6,525,157, each of which is incorporated herein by reference in its entirety. Such propylene/alpha-olefin copolymers are commercially available from The Dow Chemical Company, under the tradename VERSIFY™, or from ExxonMobil Chemical Company, under the tradename VISTAMAXX™.

In one embodiment, the ethylene acrylic acid copolymer and metallocene catalyzed polyolefin are melt-kneaded in an extruder along with water and a neutralizing agent, such as ammonia, potassium hydroxide, or a combination of the two, to form an aqueous dispersion.

In one embodiment, the present invention provides personal care compositions, comprising an aqueous dispersion comprising an ethylene acrylic acid copolymer, optionally, metallocene catalyzed polyolefin, and a silicone, provided that the silicone is not in the aqueous dispersion. Silicones include silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, preferably dimethicone, cyclopentasiloxane, cyclohexasiloxane, or a combination thereof. A preferred blend of dimethicone, Laureth-23, and C 12-15 Pareth-3 is commercially available from Dow-Corning under the tradename DOW CORNING 2-1491 Silicone Emulsion, also described as a 60% large particle size non-ionic emulsion of a blend of ultra-high molecular weight polydimethylsiloxane gum and intermediate molecular weight polydimethylsiloxane fluid. Preferably, the silicone is present in a range from about 0.1 wt % to about 5 wt %, preferably from about 0.75 wt % to about 3 wt %, and more preferably from about 1 wt % to about 2 wt %, by weight of the personal care composition.

The surfactant is a cationic, anionic, nonionic, or amphoteric surfactant, or a mixture thereof. In one embodiment, the surfactant is a nonionic/emulsifier surfactant. In one embodiment, the surfactant is a cationic surfactant, preferably behentrimonium chloride. In this embodiment, the surfactant is present in an amount from about 0.1 wt % to about 10 wt % by weight of the composition, preferably from about 0.5 wt % to about 7 wt % by weight of the composition, most preferably from about 1 wt % to about 4 wt % by weight of the composition.

In one embodiment, the surfactant is a detergent surfactant. In this embodiment, the surfactant is present in an amount from about 1 wt % to about 25 wt % by weight of the composition, preferably from about 5 wt % to about 20 wt % by weight of the composition, most preferably from about 7 wt % to about 18 wt % by weight of the composition.

Preferably, the detergent surfactant is an anionic surfactant in combination with an amphoteric surfactant. In one embodiment, the anionic surfactant is ammonium laureth sulfate, ammonium lauryl sulfate, sodium laureth sulfate, or sodium lauryl sulfate. In one embodiment, the anionic surfactant is present in an amount from about 1 wt % to about 25 wt %, preferably from about 5 wt % to about 20 wt %, more preferably from about 7 wt % to about 15 wt %, by weight of the composition.

In one embodiment, the mixture is an anionic surfactant in combination with a second surfactant that is disodium cocoamphodiacetate, decylglucoside, or cocamidopropyl betaine. In one embodiment, the second surfactant is present in an amount from about 1 wt % to about 10 wt %, preferably from about 1 wt % to about 8 wt %, more preferably from about 2 wt % to about 6 wt %, by weight of the composition.

In a preferred embodiment, the surfactant is a mixture of sodium laureth sulfate (such as is commercially available from Cognis as under the tradename STANDAPOL ES) and disodium cocoamphodiacetate (such as is commercially available from Henkel as under the tradename VELVETEX CDC). When the surfactant is a mixture of sodium laureth sulfate and disodium cocoamphodiacetate, the ratio of sodium laureth sulfate to disodium cocoamphodiacetate is in a range from about 9:1 to about 2:1, most preferably about 6:1.

In one embodiment, the composition includes citric acid to adjust the pH.

In one embodiment, the composition further comprises a cationic polymer. Cationic polymer is herein defined as a polysaccharide modified to have a positive charge, for example, cationic cellulose derivatives (including for example PQ 10, PQ 24, and PQ 67), cationic guar derivatives, cationic methacrylamido polymers, and synthetic cationic polymers, such as PQ6 and PQ7. In a preferred embodiment, the cationic polymer is cationically modified hydroxyethylcellulose, which is commercially available from The Dow Chemical Company under the tradename UCARE.

Other optional ingredients for personal care compositions of the present invention include cosmetically acceptable emollients, sunscreens, surfactants, emulsifiers, preservatives, rheology modifiers, colorants, dyes, preservatives, pH adjustors, propellants, reducing agents, fragrances, foaming agents, tanning agents, depilatory agents, flavors, astringents, antiseptics, deodorants, antiperspirants, insect repellants, bleaches, lighteners, anti-dandruff agents, adhesives, polishes, strengtheners, fillers, barrier materials, or biocides.

In some embodiments, the personal care composition further comprises an optional rheology modifier as a thickener. Examples of thickeners include polymers, for example, modified or unmodified carboxyvinyl polymers, such as the products sold under the names CARBOPOL and PEMULEN (INCI name: Acrylates/$C_{10-30}$ alkyl acrylate crosspolymer; available from Noveon), polyacrylates and polymethacrylates, such as the products sold under the names LUBRAJEL and NORGEL (commercially available from Guardian) or HISPAGEL (commercially available from Hispano Chimica), polyacrylamides, 2-acrylamido-2-methylpropane-sulfonic acid polymers and polymers, which are optionally crosslinked and/or neutralized, for instance the poly(2-acrylamido-2-methylpropane-sulfonic acid) sold by Clariant (INCI name: ammonium polyacryldimethyltauramide), emulsified crosslinked anionic polymers of acrylamide and AMPS, such as those sold under the name SEPIGEL 305 (INCI name: Polyacrylamide/C13-14 Isoparaffin/Laureth-7;

from Seppic) and under the name SIMULGEL 600 (INCI name: Acrylamide/Sodium acryloyldimethyltaurate polymer/Isohexadecane/Polysorbate 80; from Seppic), polysaccharide biopolymers, for instance xanthan gum, guar gum, carob gum, acacia gum, scleroglucans, chitin and chitosan derivatives, carrageenans, gellans, alginates, celluloses such as microcrystalline cellulose, cellulose derivatives, associative polymers, for instance associative polyurethanes, polymers comprising at least two hydrocarbon-based lipophilic chains comprising from 6 to 30 carbon atoms, separated with a hydrophilic sequence, such as the polyurethanes sold under the names SERAD FX1010, SERAD FX1100 and SERAD FX1035 (commercially available from Hüls America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACRYSOL RM 2020 (commercially available from Röhm & Haas).

Colorants include pigments, which are used especially in make-up, including metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum (for example D&C or FD&C), cochineal carmine, mica coated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/molybdenum alloy, glass substrate coated with brown iron oxide, particles comprising a stack of at least two polymer layers, for instance MIRROR GLITTER (commercially available from 3M).

Dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof. Liposoluble dyes from the list above can also optionally be used.

Preservatives include alcohols, aldehydes, methylchloroisothiazolinone and methylisothiazolinone, p-hydroxybenzoates, and in particular methylparaben, propylparaben, glutaraldehyde and ethyl alcohol.

The pH adjustors, include inorganic and organic acids and bases and in particular aqueous ammonia, citric acid, phosphoric acid, acetic acid, and sodium hydroxide.

Reducing agents include ammonium thioglycolate, hydroquinone and sodium thioglycolate.

Fragrances can be aldehydes, ketones, or oils obtained by extraction of natural substances or synthetically produced as described above. Often, fragrances are accompanied by auxiliary materials, such as fixatives, extenders, stabilizers and solvents.

Biocides include antimicrobials, bactericides, fungicides, algaecides, mildicides, disinfectants, antiseptics, and insecticides.

The amount of optional ingredients effective for achieving the desired property provided by such ingredients can be readily determined by one skilled in the art.

In a preferred embodiment, the personal care composition is a shampoo, body wash, or facial cleanser, preferably a shampoo.

In use, the personal care compositions are applied to hair or skin. In one embodiment, applying the present personal care compositions constitute a method of conditioning hair.

In one embodiment, the present invention comprises a shampoo that cleans, conditions, and increases manageability, for example exhibits improved curl retention and frizz control.

EXAMPLES

The following examples are for illustrative purposes only and are not intended to limit the scope of the present invention. All percentages are by weight unless otherwise specified.

Example 1

Personal care compositions of the present invention include aqueous dispersions comprising an ethylene acrylic acid copolymer. Examples of such aqueous dispersions include the following:

Batch A

PRIMACOR 5980i 20% ethylene acrylic acid resin (133 g), potassium hydroxide (17.2 g), and water (200 g) are placed in a 300 mL Parr reactor vessel fitted with a Cowles blade. The material is heated to 120° C. while mixing slowly. Once the set temperature is reached, the mixer is run on high (~1800 rpm) for 25 minutes. While still mixing on high, the sample is diluted with water fed into the reactor with an HPLC pump at a rate of 40 mL/min to the desired concentration of 23% solids by weight based on the amount of Primacor. Heat is removed and stirring continues until the temperature cools to at least 45° C. The Parr is then opened and the dispersion is collected.

Batch B

PRIMACOR 5980i 20% ethylene acrylic acid resin (30.7 g), potassium hydroxide (4 g), and water (92 g) are placed in a Parr reactor vessel fitted with a Cowles blade. The material is heated to about 120° C. while mixing slowly. Once the temperature is reached, the mixer is run on high (~1800 rpm) for about 25 minutes. Heat is removed and stirring continues until the temperature cools to at least 30° C.

12.9 g of this aqueous dispersion is combined with 23.9 g Zinc Pyrithione (ZPT) dispersion ((48.8% active) obtained from Arch Chemicals under the tradename ZINC OMADINE) and mixed in the Parr reactor. The material is mixed on high (~1800 rpm) at room temperature for 25 minutes. The final aqueous dispersion is then collected, affording a 4:1 ratio of ZPT:PRIMACOR.

Batch C

A 41.7% solids aqueous dispersion of ethylene acrylic acid and metallocene catalyzed polyolefin, commercially available from The Dow Chemical Company under the tradename HYPOD 8510, produced using Dow's BLUEWAVE technology.

Example 2

Exemplary personal care shampoo compositions contain the components recited in TABLE 1 on a weight/weight basis (wt. %).

TABLE 1

| | Formulation A | Formulation B |
|---|---|---|
| STANDAPOL ES-2 sodium laureth sulfate | 60.78 | 60.78 |
| VELVETEX CDC disodium cocoamphodiacetate | 6.92 | 6.92 |

TABLE 1-continued

| | Formulation A | Formulation B |
|---|---|---|
| Batch A (25%) | 0 | 1.0 |
| Batch C (41.7%) | 0.6 | 0 |
| Citric Acid (10%) | 2.1 | 2.1 |
| GLYDANT DMDM Hydantoin | 0.4 | 0.4 |
| Deionized water | q.s. | q.s. |

Combine Batch A or Batch C with base surfactants. Slowly heat to about 74° C. while mixing with an overhead stirrer (approximately 500 rpm). Continue stirring until surfactants are in solution. Cool to room temperature. Add 10% citric acid and stir about 10 minutes. Add Glydant preservative and q.s. with water to 100 g. Stir about 15 min at approximately 500 rpm.

Example 3

Comparative

Conventional personal care shampoo compositions contain the components recited in TABLE 2 on a weight/weight basis (wt. %).

TABLE 2

| | Comparative 1 | Comparative 2 | Comparative 3 |
|---|---|---|---|
| STANDAPOL ES-2 sodium laureth sulfate | 60.78 | 60.78 | 60.78 |
| VELVETEX CDC disodium cocoamphodiacetate | 6.92 | 6.92 | 6.92 |
| UCARE JR-400 hydroxyethylcellulose (1%) | 25 | 0 | 0 |
| UCARE LR-30M hydroxyethylcellulose (2%) | 0 | 12.5 | 0 |
| JAGUAR C-13S cationic guar (2%) | 0 | 0 | 12.5 |
| Citric Acid (10%) | 2.1 | 2.1 | 2.1 |
| GLYDANT DMDM Hydantoin | 0.4 | 0.4 | 0.4 |
| Deionized water | q.s. | q.s. | q.s. |

Control shampoos are prepared substantially as described in Example 2, but contain 0.3% of a conventional cationic conditioning polymer (i.e., JAGUAR C-13S guar, UCARE polymer JR400, UCARE polymer LR30M) instead of the aqueous dispersion.

Example 4

Compositions substantially according to the protocols of Examples 2 and 3 were prepared. Pre-washed and pre-hydrated tresses of European Virgin-Brown and 8-hour bleached hair (available from International Hair Importers and Products Inc.) were treated with 0.5 g of these shampoo formulations. The shampoo was worked into the hair for 1 min. and then rinsed off under running tap water at 38° C. at 0.4 gal./min. water flow.

The hair tresses were hung for wet sensory evaluation study. After the tresses were completely dried, dry sensory evaluations were conducted. Ten expert panelists trained to evaluate the performance of cosmetic products on hair were asked to evaluate comb-ability and feel in both the wet and dry stage. Each panelist evaluated a pair of tresses, one tress treated with a composition of the invention versus one treated with a comparative composition. The panelists were asked to pick one tress with superior wet and dry attributes. Brown hair results are given in TABLE 3A, bleached hair results in TABLE 3B.

TABLE 3A

| | Form. A vs. Comp. 1 | Form. A vs. Comp. 2 | Form. A vs. Comp. 3 | Form. B vs. Comp. 3 |
|---|---|---|---|---|
| Wet comb | 60 | 60 | 70 | 70 |
| Wet feel | 60 | 60 | 70 | 70 |
| Dry comb | 80 | 90 | 40 | 80 |
| Dry feel | 80 | 90 | 40 | 80 |

TABLE 3B

| | Form. A vs. Comp. 1 | Form. A vs. Comp. 2 | Form. A vs. Comp. 3 |
|---|---|---|---|
| Wet comb | 50 | 80 | 80 |
| Wet feel | 50 | 80 | 80 |
| Dry comb | 70 | 100 | 60 |
| Dry feel | 70 | 100 | 60 |

The results show that Batch A and Batch C function as efficient conditioning materials and had equal or better performance compared with leading conditioning ingredients.

In a separate evaluation, scanning electron micrographs were taken of 8 hour bleached hair washed with Formulation A (containing Batch C) with normal rinse (1 min under tap water) and excessive rinsing (1 min under tap water+dunking 30 times in a beaker of water, squeezing out water after every 5-10 dunks). Hair washed with Formulation A using normal rinsing showed particle deposition, even after blow drying. Hair washed with Formulation A using excessive rinsing did not show particles on the hair, which shows that the deposition of particles on hair washed with shampoo containing polyolefin is not substantive and can be removed from the hair with excessive rinsing.

In another evaluation, hair tresses (8 hour bleached) were washed as above using Formulation A or Comparative 3 and dried. Objective dry combing measurements were taken using a DIA-STRON device from Dia-Stron Limited, Hampshie, UK. The lower force required to pull the comb through the hair, the more conditioned the hair is. Formulation A shows as good or better dry combing force as Comparative 3 with air drying (2189 compared to 2220) and significantly better for blow drying (656 compared to 1621), signifying excellent conditioning even in the absence of a cationic polymer.

In another evaluation, hair tresses (8 hour bleached) were washed as above using Formulation A, Formulation B or Comparative 1 and dried. Very damaged hair (e.g., 8-hour bleached hair) is significantly more hydrophilic than virgin brown hair, since as hair becomes damaged, protective fatty acids are stripped from the hair making it more hydrophilic. Hydrophobicity can be used as a measure of repair by replacing the fatty acid coating and indicates deposition of a substance on the hair during shampooing. On bleached hair, Formulation A and Formulation B have a hydrophobicity (determined by advancing contact angle) of 55.8±11.5, 85.3±0.85, respectively, compared to 45.2±4.40 for untreated 8 hour bleached hair. Comparative 1 did not increase hydrophobicity, thus, it is believed that the mechanism for hair conditioning of the cationic polymer is different from that of the inventive formulations.

Example 5

Exemplary personal care rinse-off conditioning compositions contain the components weight/weight basis (wt. %) recited in TABLE 4.

TABLE 4

| | | Formulation C |
|---|---|---|
| A | PROCOL CS-20-D Cetearyl alcohol (and) ceteareth-20 | 3.0 |
| | JEECHEM S-13 Stearamidopropyl dimethylamine | 0.8 |
| | MACQUAT BTMC 85 (85%) Behentrimonium chloride | 2.4 |
| | Stearyl alcohol | 1.5 |
| B | Deionized water | 86.9 |
| | Methyl Gluceth -10 | 1.0 |
| C | GLYDANT DMDM Hydantoin | 0.4 |
| D | Batch A (25%) | 4.0 |
| E | Citric acid (50%) | q.s. to pH 4-5 |

Combine Phase A ingredients, mix, and heat to 75° C. under stiffing. In a separate reaction vessel, phase B ingredients are combined, mixed and heated to 75° C. under stiffing. Phase B is added to phase A at 75° C. under stirring at 470 rpm. The reaction mixture is allowed to cool to room temperature while stiffing. Glydant is added at 35° C. Batch A is added to the mixture at room temperature and mixed in for 20 min. pH of the formulation was adjusted to 4-5 using 50% citric acid as needed.

Example 6

Comparative

Comparative personal care rinse-off conditioning compositions contain the components weight/weight basis (wt. %) recited in TABLE 5.

TABLE 5

| | | Comparative 4 |
|---|---|---|
| A | PROCOL CS-20-D Cetearyl alcohol (and) ceteareth-20 | 3.0 |
| | JEECHEM S-13 Stearamidopropyl dimethylamine | 0.8 |
| | MACQUAT BTMC 85 (85%) Behentrimonium chloride | 2.4 |
| | Stearyl alcohol | 1.5 |
| B | Deionized water | 89.9 |
| | Methyl Gluceth -10 | 1.0 |
| C | DC 345 Cyclopentasiloxane (and) cyclohexasiloxane | 1.0 |
| | GLYDANT DMDM Hydantoin | 0.4 |
| D | Citric acid (50%) | q.s. to pH 4-5 |

Compositions are prepared as in Example 5, except that Batch A is not present and Glydant and DC 345 are added at 35° C.

Example 7

Compositions substantially according to the protocols of Examples 5 and 6 were prepared. Pre-washed and pre-hydrated ten inch long hair tresses of European single-bleached hair (available from International Hair Importers and Products Inc. (Floral Park, N.Y.)) were treated with 0.1 g of the conditioner formulations, which was worked into the hair for 1 min. and then rinsed off under running tap water at 38° C. and 0.4 gal./min. water flow.

The hair tresses were hung for wet sensory evaluation study. After the tresses were completely dried, dry sensory evaluations were conducted. Ten expert panelists trained to evaluate the performance of cosmetic products on hair were asked to evaluate comb-ability and feel in both the wet and dry stage. Each panelist evaluated a pair of tresses, one tress treated with Formulation C of the present invention versus one treated with a Comparative 4 composition. The panelists were asked to pick one tress that combed easier and felt more slippery/smoother (wet) or silkier/softer (dry). The inventive formulation was found similar to the comparative formulation in all categories tested (differences not statistically significant on wet and dry hair), showing the inventive formulation displayed similar performance to silicones.

Example 8

Exemplary personal care leave-on conditioner compositions contain the components recited in TABLE 6 on a weight/weight basis (wt. %).

TABLE 6

| | | Formulation E |
|---|---|---|
| A | Deionized water | 85.6 |
| | CELLOSIZE PCG-10 Hydroxyethyl cellulose | 0.5 |
| | PROTAQUAT CT-29 Cetrimonium chloride | 3.4 |
| B | Cetyl alcohol | 2.0 |
| | Stearyl alchohol | 3.0 |
| | Hydrogenated vegetable oil | 1.0 |
| C | Panthenol | 0.1 |
| | Batch A (25%) | 4.0 |
| | GLYDANT DMDM Hydantoin | 0.4 |
| D | Citric acid (50%) | q.s. to pH 4-5 |

CELLOSIZE PCG-10 is sprinkled into rapidly agitating, room temperature water. Once uniform, the solution is heated to 60° C. and cetrimonium chloride is added to the mixture and stirred until dissolved. The pre-mix is then heated to 75° C. under stirring. In a separate reaction vessel, fatty alcohols of phase B are combined, mixed until uniform and heated to 75° C. under stirring. Vegetable oil is added in under stiffing. Phase B is added to phase A at 75° C. under stirring at 470 rpm. The reaction mixture is allowed to cool while stirring. Phase C ingredients are added at 35° C., and pH of the formulation was adjusted to 4-5 using 50% citric acid as needed.

Example 9

Exemplary personal care shampoo compositions contain the components recited in TABLE 7 on a weight/weight basis (wt. %).

TABLE 7

| | Formulation F |
|---|---|
| Standapol ES-2 sodium laureth sulfate (25.5%) | 39.21 |
| Standapol WAQ sodium lauryl sulfate (25.5%) | 23.52 |
| PROTAMIDE CME Cocamide MEA | 2.00 |
| LEXEMUL EGDS pearlizing agent | 1.50 |
| Cetyl Alcohol | 0.60 |
| DC 2-1491 Dimethicone Emulsion (60%) | 1.67 |
| Batch B (25%) | 5.00 |
| NaCl | 1.0 |
| GLYDANT DMDM Hydantoin | 0.4 |
| Deionized water | q.s |

Combine Batch B with base surfactants. Slowly heat to about 74° C. while mixing with an overhead stirrer (approximately 500 rpm). Continue stirring until surfactants are in solution. Cool to room temperature. Add 10% citric acid and stir about 10 minutes. Add Glydant preservative and q.s. with water to 100 g. Stir about 15 min at approximately 500 rpm.

Example 10

Comparative

Conventional personal care shampoo compositions contain the components recited in TABLE 8 on a weight/weight basis (wt. %).

TABLE 8

|  | Comparative 5 |
|---|---|
| Standapol ES-2 sodium laureth sulfate (25.5%) | 39.21 |
| Standapol WAQ sodium lauryl sulfate (25.5%) | 23.52 |
| PROTAMIDE CME Cocamide MEA | 2.00 |
| LEXEMUL EGDS pearlizing agent | 1.50 |
| Cetyl Alcohol | 0.60 |
| DC 2-1491 Dimethicone Emulsion (60%) | 1.67 |
| ZINC OMADINE FPS dispersion (48.8%) | 2.05 |
| NaCl | 1.0 |
| GLYDANT DMDM Hydantoin | 0.4 |
| Deionized water | q.s |

Control shampoo is prepared substantially as described in Example 9, but contains commercial ZPT dispersion available from Arch Chemical as ZINC OMADINE FPS dispersion.

Example 11

Compositions substantially according to the protocols of Examples 9 and 10 were prepared and applied to virgin brown hair. The tresses were tested substantially according to the methods described in Example 4, and Formulation F deposits at least 25% more zinc onto hair than the Comparative 5 composition (17.1 ppm vs. 13.6 ppm).

Example 12

Exemplary personal care shampoo compositions contain the components recited in TABLE 9 on a weight/weight basis (wt. %).

TABLE 9

|  | Formulation G | Formulation H |
|---|---|---|
| STANDAPOL ES-2 sodium laureth sulfate (25%) | 60.78 | 60.78 |
| VELVETEX CDC disodium cocoamphodiacetate (38%) | 6.92 | 6.92 |
| Batch A (25%) | 0 | 8.0 |
| Batch C (41.7%) | 4.8 | 0 |
| Ethylene glycol distearate (EDGS) | 2.0 | 0 |
| Citric Acid (10%) | 2.1 | 2.1 |
| KATHON preservative | 0.4 | 0.4 |
| Deionized water | q.s. | q.s. |

Slowly heat base surfactants to about 74° C. while mixing with an overhead stirrer (approximately 500 rpm). Continue stirring until surfactants are in solution. Add Ethylene glycol distearate, if present, and stir until dissolved. Cool to room temperature. Add Batch A or Batch C. Add 10% citric acid and stir about 10 minutes. Add preservative and q.s. with water to 100 g. Stir about 15 min at approximately 500 rpm.

Example 12

Comparative

Conventional personal care shampoo compositions contain the components recited in TABLE 10 on a weight/weight basis (wt. %).

TABLE 10

|  | Comparative 6 | Comparative 7 |
|---|---|---|
| STANDAPOL ES-2 sodium laureth sulfate (25%) | 60.78 | 60.78 |
| VELVETEX CDC disodium cocoamphodiacetate (38%) | 6.92 | 6.92 |
| Ethylene glycol distearate (EDGS) | 2.0 | 0 |
| Citric Acid (10%) | 2.1 | 2.1 |
| KATHON preservative | 0.4 | 0.4 |
| Deionized water | q.s. | q.s. |

Slowly heat base surfactants to about 74° C. while mixing with an overhead stirrer (approximately 500 rpm). Continue stirring until surfactants are in solution. Add Ethylene glycol distearate, if present, and stir until dissolved. Cool to room temperature. Add 10% citric acid and stir about 10 minutes. Add preservative and q.s. with water to 100 g. Stir about 15 min at approximately 500 rpm.

Example 13

Compositions substantially according to the protocols of Examples 11 and 12 were prepared. Pre-washed and pre-hydrated ten inch long hair tresses of European Virgin Brown and 8-hour bleached hair (available from International Hair Importers and Products Inc. (Floral Park, N.Y.)) were treated with 0.5 g of the formulations, which was worked into the hair for 1 min. and then rinsed off under running tap water at 38° C. and 0.4 gal./min. water flow.

One group of the hair tresses were dried in an oven at 38° C. After the tresses were completely dried, they were curled using a curling iron for one minute. The curls were released and photographs of the curled tresses were taken for evaluation.

Another group of the hair tresses were roller curled by diagonally applying wet hair onto a 65 mm×20 mm curler, held in place with two large bobby pins. These were air dried at ambient temperatures for 3 days, then placed in a 45° C. oven for one hour to ensure they were thoroughly dried. Curlers were then removed and the curled hair tresses were placed in a high humidity chamber (25° C., 90% relative humidity) for 24 hours. The curled tresses were removed from the humidity chamber and photographs of the curled tresses were taken for evaluation.

Fifteen expert panelists trained to evaluate the performance of cosmetic products on hair were asked to evaluate side by side photographs of Formulation G versus Comparative 6 and Formulation H versus Comparative 7 for curl retention and frizz control from both the dry curl and wet curl procedures.

Fifteen out of fifteen of the expert panelists expressed a preference for Formulation G over Comparative 6, in other words, the inventive composition was unanimously determined to display better curl retention and frizz control than the conventional formulation in both dry curl and wet curl tests. Fifteen out of fifteen of the expert panelists expressed a preference for Formulation H over Comparative 7, in other words, the inventive composition was unanimously determined to display better curl retention and frizz control than the conventional formulation in both dry curl and wet curl tests.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this document are hereby incorporated herein by reference, in their entireties.

The invention claimed is:

1. A personal care composition, comprising:
an aqueous dispersion comprising an ethylene acrylic acid copolymer, said aqueous dispersion being present in the personal care composition in an amount from about 0.25 wt % to about 5 wt % by weight of the composition; and
about 7 wt % to about 18 wt %, by weight of the composition, of a detergent surfactant,
wherein the personal care composition is a shampoo, a rinse-off conditioner, a leave-in conditioner, or a body wash; and
wherein the ethylene acrylic acid copolymer is present in a range from about 10 wt % to about 30 wt % by weight of the aqueous dispersion.

2. The personal care composition of claim 1, provided that the personal care composition is not an emulsion.

3. The personal care composition of claim 1, wherein the aqueous dispersion comprises at least one anti-dandruff active, sunscreen active, pigment, fragrance, botanical, amino acid, or vitamin.

4. A personal care composition, comprising:
an aqueous dispersion comprising an ethylene acrylic acid copolymer and a metallocene catalyzed polyolefin, said aqueous dispersion being about 30 wt % to about 50 wt % solids; and
at least one cosmetically acceptable surfactant, emollient, or cosmetic active,
wherein the personal care composition is a shampoo, a rinse-off conditioner,
a leave-in conditioner, or a body wash; and
wherein the ethylene acrylic acid copolymer is present in a range from about 1 wt % to about 25 wt % by weight of the aqueous dispersion.

5. The personal care composition of claim 4, wherein the metallocene catalyzed polyolefin comprises at least one of ethylene/octene copolymers, ethylene/butene copolymers, ethylene/hexene copolymers, ethylene/propylene or ethylene/butene/hexene terpolymers.

6. The personal care composition of claim 4, wherein the ethylene acrylic acid copolymer and metallocene catalyzed polyolefin is in a polymer ratio of about 40:60 to about 15:85.

7. The personal care composition of claim 1, wherein the aqueous dispersion is present in a range from about 0.05 wt % to about 10 wt %.

8. The personal care composition of claim 1, further comprising a silicone, provided that the silicone is not in the aqueous dispersion.

9. The personal care composition of claim 4, wherein the surfactant is present and is a detergent surfactant.

10. The personal care composition of claim 4, wherein the surfactant is present and is a nonionic surfactant.

* * * * *

UNITED STATES PATENT AND TRADEMARK OFFICE
CERTIFICATE OF CORRECTION

| | |
|---|---|
| PATENT NO. | : 8,771,657 B2 |
| APPLICATION NO. | : 12/882325 |
| DATED | : July 8, 2014 |
| INVENTOR(S) | : Susan L. Jordan and Tatiana V. Drovetskaya |

It is certified that error appears in the above-identified patent and that said Letters Patent is hereby corrected as shown below:

In the Specification:

Column 9, lines 21, 22, and 25: replace "stiffing" with "stirring".
Column 10, line 39: replace "stiffing" with "stirring".
Column 11, line 63: replace "stiffing" with "stirring".
Column 12, line 22: replace "stiffing" with "stirring".

Signed and Sealed this
Thirtieth Day of September, 2014

Michelle K. Lee
*Deputy Director of the United States Patent and Trademark Office*